(12) United States Patent
Schmidt

(10) Patent No.: US 6,480,747 B2
(45) Date of Patent: Nov. 12, 2002

(54) CARDIAC ELECTRODE CATHETER AND METHOD OF MANUFACTURING SAME

(75) Inventor: John A. Schmidt, Durango, CO (US)

(73) Assignee: Quetzal Biomedical, Inc., Durango, CO (US)

(*) Notice: Subject to any disclaimer, the term of this patent is extended or adjusted under 35 U.S.C. 154(b) by 0 days.

(21) Appl. No.: 09/761,333

(22) Filed: Jan. 16, 2001

(65) Prior Publication Data

US 2002/0095202 A1 Jul. 18, 2002

(51) Int. Cl.$^7$ .................................................. A61N 1/05
(52) U.S. Cl. ....................................................... 607/122
(58) Field of Search ................................. 607/122, 123

(56) References Cited

U.S. PATENT DOCUMENTS

| | | | |
|---|---|---|---|
| 3,825,015 A | 7/1974 | Berkovits | 128/404 |
| 3,995,623 A | 12/1976 | Blake et al. | 128/2.06 E |
| 4,172,451 A | 10/1979 | Kline | 128/642 |
| 4,522,212 A | 6/1985 | Gelinas et al. | 128/642 |
| 4,573,473 A | 3/1986 | Hess | 128/642 |
| 4,699,147 A | 10/1987 | Chilson et al. | 128/642 |
| 5,471,982 A | 12/1995 | Edwards et al. | 128/642 |
| 5,545,205 A | 8/1996 | Schulte et al. | 607/123 |
| 5,800,498 A | 9/1998 | Obino et al. | 607/123 |
| 5,997,526 A | 12/1999 | Giba et al. | 604/531 |
| 6,055,457 A | 4/2000 | Bonner | 607/126 |
| 6,106,522 A | * | 8/2000 | Fleischman et al. |

OTHER PUBLICATIONS

John J. Gallagher et al., Techniques of Intraoperative Electrophysiologic Mapping, The American Journal of Cardiology, vol. 49, Jan. 1982.

A Protocol for the Determination of Absorbed Dose From High–Energy Photon and Electron Beams, Task Group 21, Radiation Therapy Committee, American Association of Physicists in Medicine, *Medical Physics*, vol. 10, No. 6, Nov./Dec. 1983, pp. 741–771.

The Quality Factor in Radiation Protection, *International Commission on Radiation Units and Measurements, Report 40*, Apr. 4, 1986 (First Reporting: Aug. 1993).

Marco Zaider et al., Microdosimetry and Its Application to Biological Processes, *Radiation Dosimetry Physical and Biological Aspects*, Plenum Press, New York, 1986, pp. 171–239.

* cited by examiner

*Primary Examiner*—Scott M. Getzow
(74) *Attorney, Agent, or Firm*—Gottlieb, Rackman & Reisman, P.C.

(57) ABSTRACT

An electrode catheter used in an endocardial procedure to map cardiac electrical activity, heart wall position, heart wall motion and tissue viability. The electrode catheter has a flexible geometric shape for mapping any cardiac chamber and can be rotated within the chamber without being re-deployed. The electrode catheter is made from joining a tube with 4 to 256 wire leads having terminal ends and coiled electrodes. The tube either has holes or a longitudinal slit so that the coiled electrodes can protrude from the central cavity of the tube. The electrode catheter ends with a tip member that is attached to the tube by a swivel connector. The tip member has tines to allow for temporary stability when in contact with a cardiac wall. The electrode catheter is conformed to a flexible shape using a jig and heating process.

47 Claims, 8 Drawing Sheets

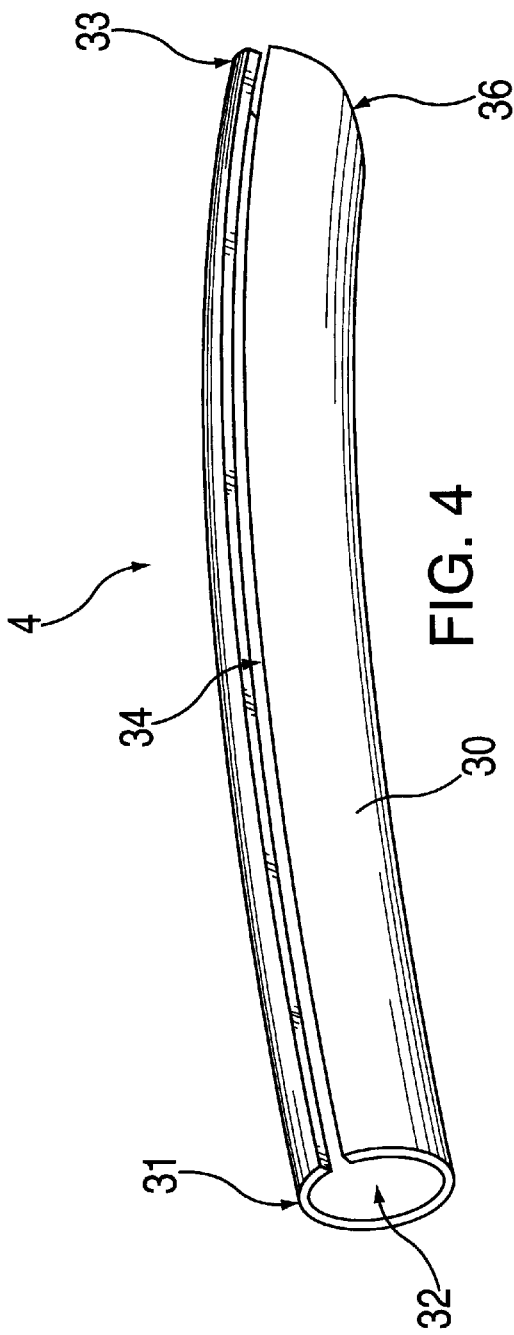
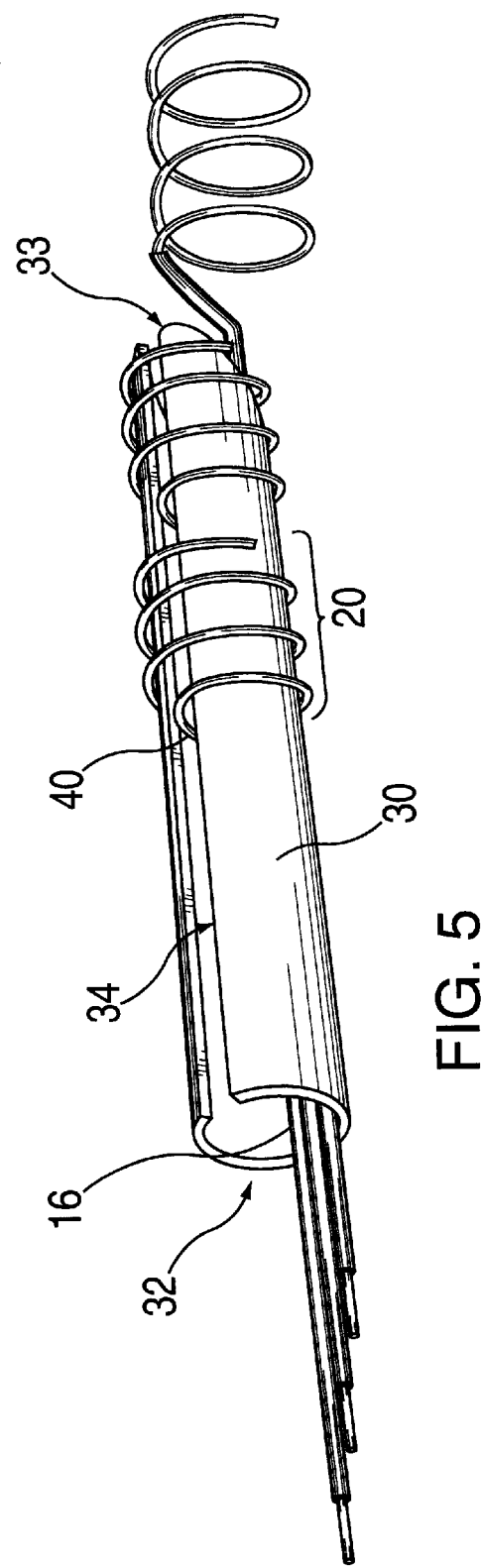

CARDIAC ELECTRODE CATHETER AND METHOD OF MANUFACTURING SAME

BACKGROUND OF INVENTION

1. Field of Invention

This invention relates to catheters or to electrodes arranged and constructed to be inserted into a body cavity. More specifically, the invention involves a catheter containing a large number of electrodes that can be inserted into a patient's heart to stimulate map cardiac electrical activity, heart wall position, heart wall motion and tissue viability for purposes of medical diagnosis and treatment of congestive heart failure, Bradycardia or tachyarrhythmias. The catheter may be used for other purposes as well. The invention also includes methods for manufacturing the device.

2. Background Art

Cardiovascular disease is the leading cause of death in the United States, Europe and Japan claiming more lives each year than all other diseases combined. The prevalence of this disease has prompted the development of numerous methods and devices to diagnose and treat various cardiac problems. One such device which aids in the diagnosis and treatment of heart disease is the electrode catheter.

In general, various types of catheters containing electrodes have been used to perform endocardial procedures for treatment and diagnosis of cardiac related problems. Examples of these devices include the stimulation catheter of Berkovits U.S. Pat. No. 3,825,015, the flow directed catheter of Blake et. al. U.S. Pat. No. 3,995,623, the multi-contact plunge electrode of Kline U.S. Pat. No. 4,172,451, the defibrillating catheter of Schulte et al. U.S. Pat. No. 5,545,205, the implantation catheter of Obino et al. U.S. Pat. No. 5,800,498 and the pacing lead delivery catheter of Bonner U.S. Pat. No. 6,055,457.

More specifically, in the diagnosis of cardiac conditions, electrode catheters have been used to map cardiac electrical activity. This mapping procedure is useful for the detection and treatment of conduction abnormalities and heart tissue deficiencies. Some cardiac mapping procedures are described in the article entitled: "Techniques of Intraoperative Electrophysiologic Mapping" in the American Journal of Cardiology, by John J. Gallagher, et al. which appeared in Volume 49 pages 221–240 January of 1982.

During a typical mapping procedure, a cardiac map is generated by recording the electric signals from the heart and depicting them spatially as a function of time. In an endocardial procedure, an electrode catheter is inserted into a chamber of the heart to measure signals directly by contact with the inside walls of the chamber. Accordingly, the number and placement of electrodes on or within the catheter is an important design consideration for maximizing effectiveness and efficiency for this internal procedure.

Several prior art electrode catheters have been used to generate cardiac maps. Hess U.S. Pat. No. 4,573,473 teaches a catheter with four electrode contacts on a flat planar surface. Gelinas et al. U.S. Pat. No. 4,522,212 teaches a catheter with three or more separated flexible leg electrodes. Chilson U.S. Pat. No. 4,699,147 and Edwards U.S. Pat. No. 5,471,982 define catheters with flexible electrodes that form a basket when extended. Giba et al. U.S. Pat. No. 5,997,526 discloses a shape memory catheter having electrode plates or bands. Unfortunately, such prior art devices are hard to deploy and complicated to manipulate. These difficulties often result in numerous unsuccessful treatment attempts as well as time consuming procedures.

OBJECTIVE AND SUMMARY OF THE INVENTION

In view of prior art deficiencies, an objective of the present invention is to design an improved cardiac electrode catheter for mapping cardiac electrical activity, heart wall position, heart wall motion and tissue viability.

It is also an objective to design an electrode catheter that is easily deployed, unobtrusive and highly maneuverable.

It is a further objective to provide a catheter and methods of producing the same having a large number of electrodes.

Additional objectives will be apparent from the following description of the invention.

Consistent with these objectives, a catheter constructed in accordance with this invention comprises a collection of wire leads disposed in a flexible tube. Each wire lead has a terminal end, an insulated portion and a non-insulated coiled electrode. The continuous coiled electrode preferably has at least one but no more than twenty-five turns. To prevent the coils from unraveling, each coiled electrode may be glued or fused together, for example, by a knitting or fusing procedure. Each wire lead in the collection is longitudinally staggered so that any one coiled electrode is close to but does not come in contact with the coiled electrode of any other wire lead. The tube is relatively narrow and has a proximal end and a distal end. The tube encloses the insulated portions of the collection of wire leads. Starting at the distal end of the tube, the coiled electrode of each wire lead protrudes from the tube at predetermined longitudinal positions and coils around the exterior of and is attached to the tube. The ends of the collection of wire leads protrude from the proximal end of the tube and are coupled to a suitable connector for connection to an apparatus which may be used to map the cardiac tissues, to monitor the condition of the heart, to apply appropriate therapy, etc. The electrode catheter has a tip member with flexible tines that is attached to the distal end of the tube by a swivel member. The fully assembled catheter can be shaped into various geometric configurations. In the preferred embodiment the catheter has a spiral form that correlates with the shapes of the internal chambers of the heart.

Several different tube configurations may be used in the catheter. In one embodiment, the tube has a longitudinal slit extending along its length, and is tapered on its distal end. The collection of wire leads is installed into the tube by opening the slit and inserting the collection of wires down the length of the tube so that the tube encompasses the insulated mid portions of the wire leads. Simultaneously, the tapered distal end of the tube is inserted through the coiled ends of the wire leads with the coiled end protruding out of the tube through the longitudinal slit.

In another embodiment, the tube has holes drilled through its exterior surface that are just large enough to accommodate the wire lead. The holes are drilled into the tube at an angle with respect to its longitudinal axis and may be in a generally helical pattern around the tube. The insulated portion of a wire lead is inserted into each hole starting with the terminal end. The entire wire lead is moved into the tube until only the coiled end is exposed. The installation of the wire leads may be assisted by pressurized air flow or fluid flow forced down the length of the tube from the distal end. The catheter can also be assembled by using a combination of the above listed methods.

A catheter made in accordance with this invention may also have a separate elongated cavity extending the length of the tubing reserved for a stylet. The stylet is used to implant the lead into the heart in the same manner as a standard pacemaker lead is implanted. The stylet is a solid metal or polymer rod small enough to fit inside the lead.

The stylet is long enough to extend from the insertion point on the proximal end of the lead to the distal tip. When inserted into the lead, the stylet serves to both stiffen and straighten the lead. Because the stylet straightens the lead (from it's preformed shape) the lead passes more easily through the veins. When the stylet is removed the lead deploys into the selected chamber of the heart.

As it will be clear from the detailed description, the catheter can be used to treat congestive heart failure or a number of conduction abnormalities of the heart such as CHF, Bradycardia, Tachycardia. For example, the catheter can be used to sequentially pace the heart of CHF patients so that a near normal contraction of the muscle takes place. This provides better contraction and increased blood flow.

For patients suffering from Bradycardia, the multi-electrode catheter allows the optimal location(s) within a heart chamber to be paced. Currently, leads are placed in the apex of the right ventricle and pacing from this location has detrimental long term effects on the heart muscle. The catheter of this invention will allow the doctor to select the best pacing site for each patient.

Fast heartbeats (tachyarrhythmias and fibrillations) can be treated with the multielectrode catheter by either preventing or terminating the event. Prevention uses the system's ability to identify and triangulate the location of a given event and pace the heart in areas that will disrupt the propagation of the arrhythmia. Termination involves delivering low voltage pulses to large areas of the heart, either simultaneously or in rapid sequence. These pulses will have the same effect as a high energy defibrillation pulse in capturing the heart and re-synchronizing the electrical activity of the heart but without the complications of a high energy shock.

Because this catheter is placed in the right side of the heart it allows more consistent and easier lead placement to pace the left ventricle; from the right ventricular outflow tract or the ventricular septum. The lead does not have to be threaded down the great cardiac vein with all of the associated complications and time consuming procedures.

DESCRIPTION OF DRAWINGS

FIG. 4 shows one embodiment of a tube used in the assembly of the electrode catheter of FIG. 1;

FIG. 5 shows a partially assembled electrode catheter using the tube of FIG. 4;

DETAILED DESCRIPTION OF THE INVENTION

Figure 1:
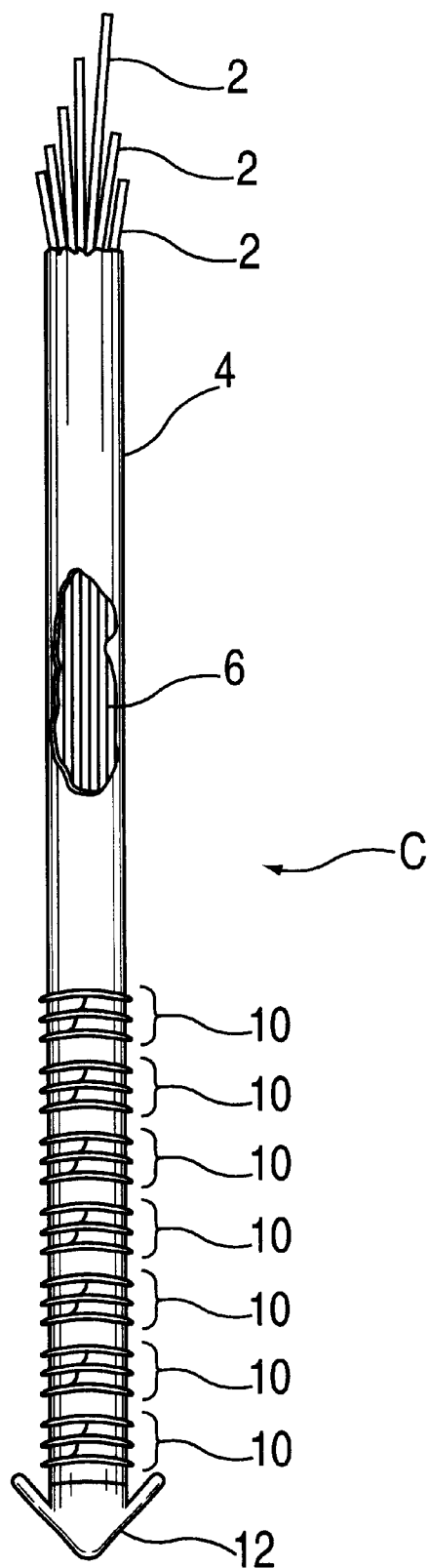
FIG. 1 is depicts an elevational view of an embodiment of an electrode catheter constructed in accordance with this invention.

FIG. 1 depicts an electrode catheter C constructed in accordance with this invention. The figure generally shows the assembled elements of the catheter C. The electrode catheter C includes a collection of wire leads 6 each having opposed terminal ends 2 and coiled electrodes 10. The collection of wire leads 6 is encased in a tube 4. The tube 4 has a tip member 12.

Figure 2:
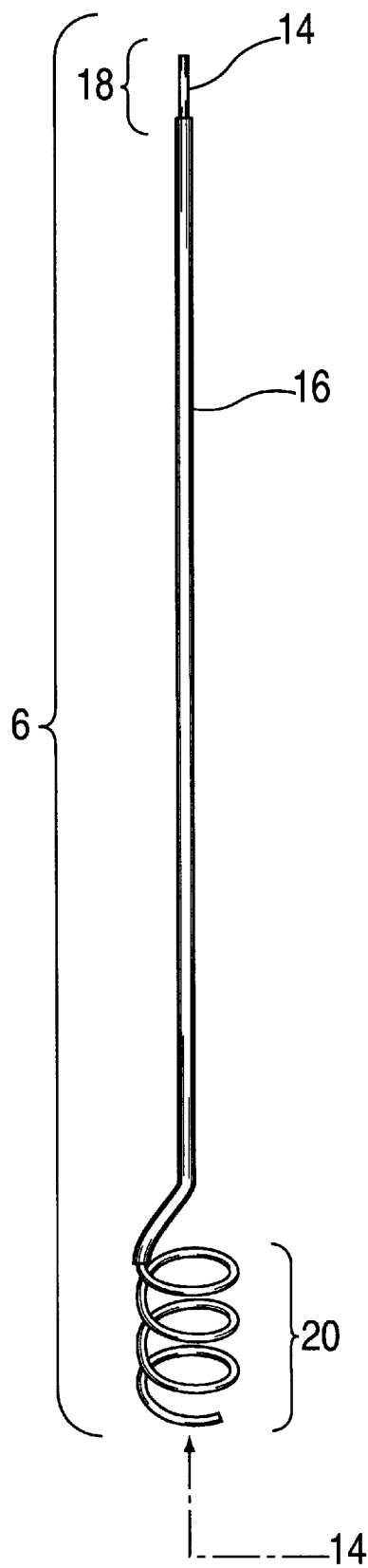
FIG. 2 depicts a single continuous wire lead for the catheter of FIG. 1.

FIG. 2 shows a single wire lead 6. The wire lead 6 is made from an electrical conductor 14. In the preferred embodiment, the electrical conductor is a MP35N, platinum or stainless steel wire with a 0.001 inch diameter. The wire lead has an insulated portion 16. The insulating material in the preferred embodiment has a thickness of 0.001 inch or less. Such insulating materials may include ETFE, PFA, polyamide or polyurethane. Generally, the length of the wire lead must be coordinated with the length of the tube 4.

The wire lead has a terminal end 18. The terminal end 18 is attached to a connector for coupling electrically to a cardiac device so that the catheter can be used for the purposes described above.

The wire lead also has a coiled electrode 20 at the opposite end from the terminal end 18. The coiled electrode 20 is formed of several helical spirals or coils of the conductor 14. The diameter of each coil is sufficiently large to wrap around the exterior surface of the tube 4 of the catheter C. In the preferred embodiment, the coiled electrode has between one and ten coils.

Figure 3:
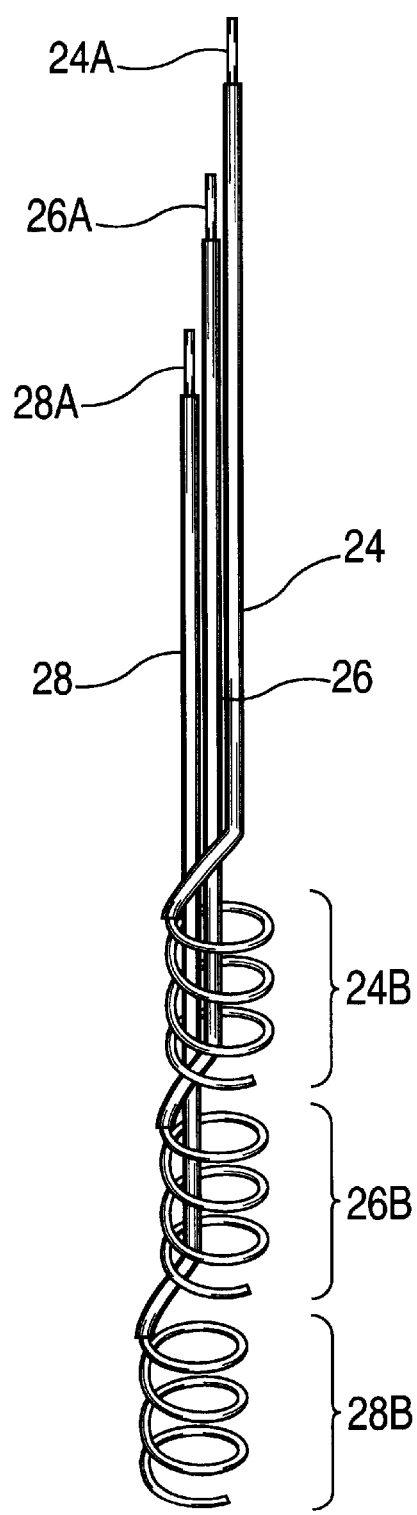
FIG. 3 shows the staggering of a collection of wire leads for the catheter of FIG. 1.

Each catheter C requires a plurality of wire leads. FIG. 3 depicts several wire leads 24, 26, 28, each having the same structure as wire lead 6. The first wire lead 24, second wire lead 26, and third wire lead 28 are lined up in parallel fashion with the terminal ends 24A, 26A, 28A on one end and the coiled electrodes 24B, 26B, 28B on the other. To prevent a short or electrical interference between any two electrodes, the coiled electrodes 24B, 26B, 28B are staggered or axially offset so that the first coiled electrode 24B associated with the first wire lead 24 is adjacent to but does not overlap or come in contact with any other coiled electrode in the collection of electrodes. Similarly, the second coiled electrode 26B of the second wire lead 26 and the third coiled electrode 26B of the third wire lead 26 does not overlap or come in to contact with any other coiled electrode.

In the preferred embodiment of the electrode catheter, 128 wire leads are used. Accordingly, 128 coiled electrodes are staggered in a configuration similar to the three wire lead collection portrayed in FIG. 3. However, the number of wire leads may be changed for example from 4 to 256, etc.

FIG. 4 depicts the tube used in the assembly of the electrode catheter C. The tube 4 has a proximal end 31 and a distal end 33. The tube is a hollow cylindrical sheathing with an exterior surface 30 and defines a longitudinal central cavity 32. The diameter of the cavity 32 of the tube must be large enough to contain the collection of wire leads 6. The tube 4 has a longitudinal slit 34 and a taper 36 on its distal end 33. The tube is manufactured from a material that is flexible and may have a shape memory that will force the tube 4 to return to a predefined shape after the tube is distorted. In the preferred embodiment, the tube is made from a shapeable thermoplastic polyurethane material and has an internal diameter of 0.045 inches and an external diameter of 0.060 inches. The length of the tube 4 is selected to insure that it can be used to position the electrodes in a patient's heart, or for any other desired purpose.

FIG. 5 depicts a portion of a partially assembled electrode catheter C using the tube 4 of FIG. 4 and a collection of wire leads 6 of FIG. 3. The tube 4 is combined with the collection of wire leads 6 so that the insulated portion 16 of each wire lead 6 will be contained within the cavity 32 of the tube 4. During assembly, the tapered distal end 36 extends through the coiled electrode 20 of each wire lead 6. The coiled electrodes 20 are disposed outside the cavity 32 and extend through the longitudinal slit 34.

The catheter C of FIG. 5 is assembled by positioning all the leads adjacent to each other and then pushing the tube 4 through the electrodes 20 as shown. The diameter of coils of the coiled electrodes 20 is selected to be slightly smaller than the outside diameter of tube 4 so that an interference fit is formed between the electrodes and the tube.

Figure 6:
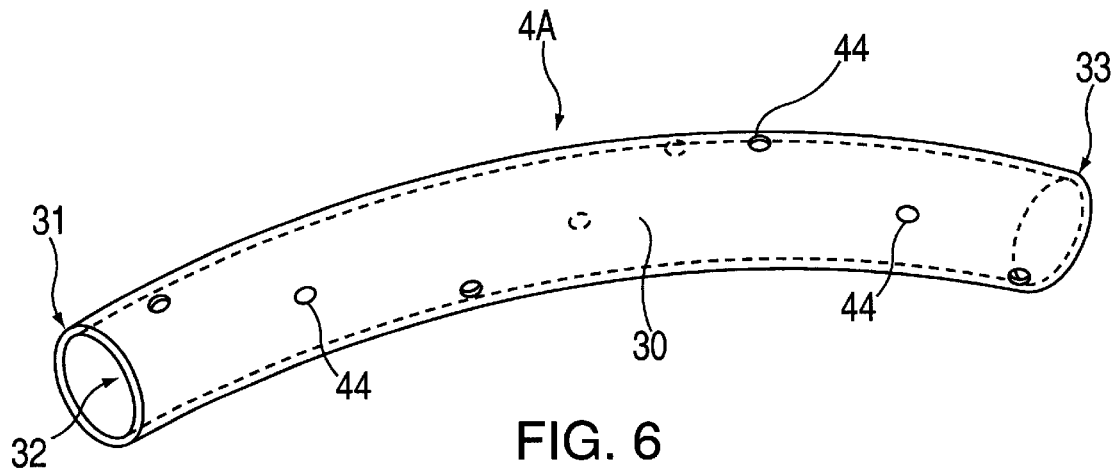
FIG. 6 shows a second embodiment of the tube for the electrode catheter of FIG. 1.
Figure 7:
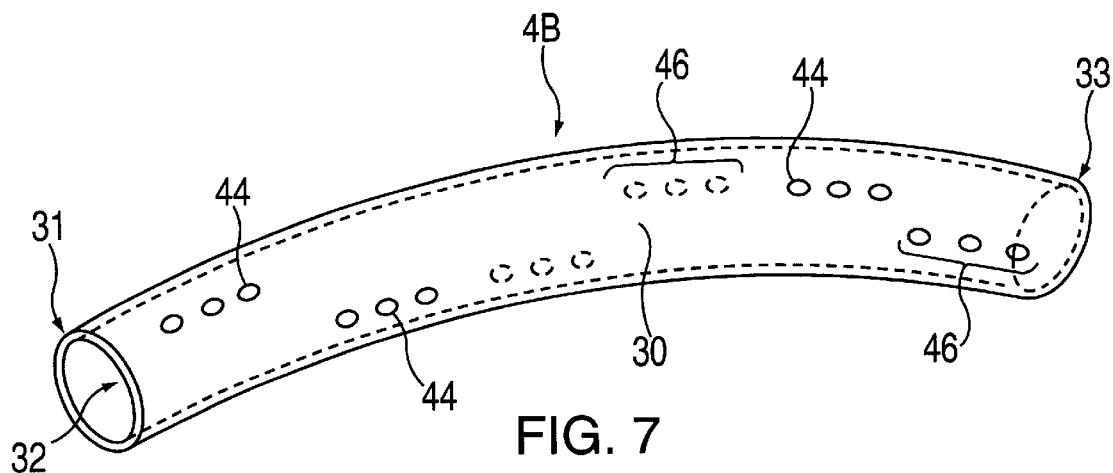
FIG. 7 shows a third embodiment for the tube for the catheter of FIG. 1.

FIGS. 6 and 7 depict alternative embodiments of the tube used in the assembly of the electrode catheter C. In these figures, tubes 4A, 4B having a proximal end 31, distal end 33, exterior surface 30, cavity 32 and generally being made from the same material and having the same internal and external diameters as the tube 4. However, these embodiments of the tubes 4A, 4B have holes 44, 46. The holes 44, 46 each extend at an angle through the exterior surface 30 and into the central cavity 32. The holes 44, 46 have a diameter sufficiently large to receive one of the wire leads 6 including the insulating material 16.

Due to the large number of holes 44, 46 needed to receive the wire leads and a need to keep the coiled electrodes closely placed, the holes 44 are disposed in patterns intended to preserve the structural integrity of the tube by increasing the separation between the holes and minimizing stress. FIG. 6 shows one such pattern. Tube 4A has holes 44 arranged generally around the tube. In FIG. 7, sets of three or more holes 46 in tube 4B are arranged in a generally helical pattern. Each set includes holes 46 arranged in a line parallel with the longitude axis of the tube.

Figure 8:
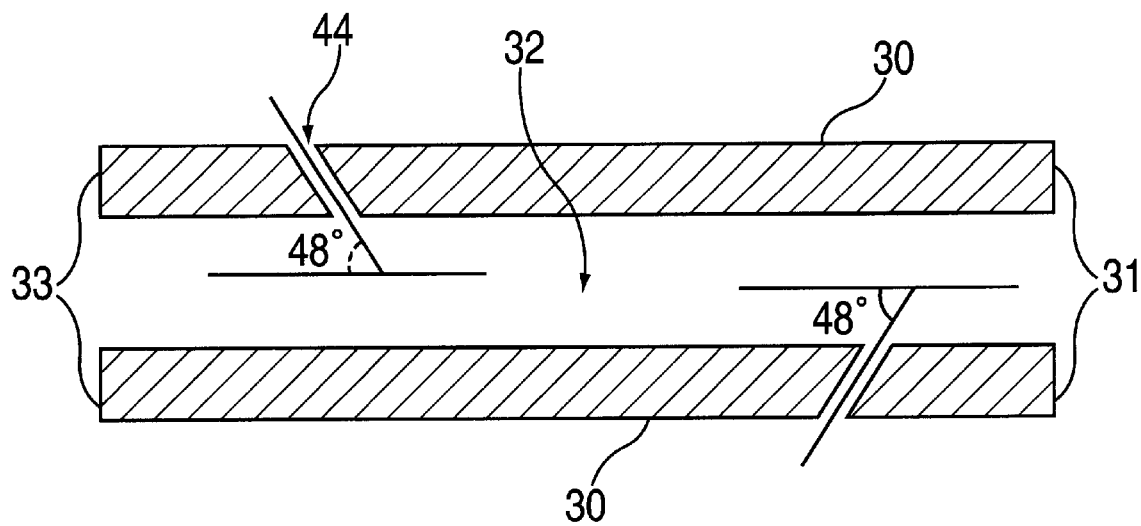
FIG. 8 shows a cross-sectional view of the tube of FIG. 6 or 7.

Details of the holes 44, 46 are depicted in FIG. 8. The holes 44, 46 are angled to reduce the resistance encountered when the wire leads are inserted through the holes 44, 46. The holes 44, 46, are preferably drilled through the exterior surface 30 to the central cavity 32, each hole being angled away from the distal end 33 of the tube and towards the proximal end 31. In the preferred embodiment, the angle 48 formed by the central axis of the hole 44 with the central longitudinal axis of the cavity 32 of the tube is about 60 degrees. This angle may vary from 15 to 90 degrees.

Figure 9:
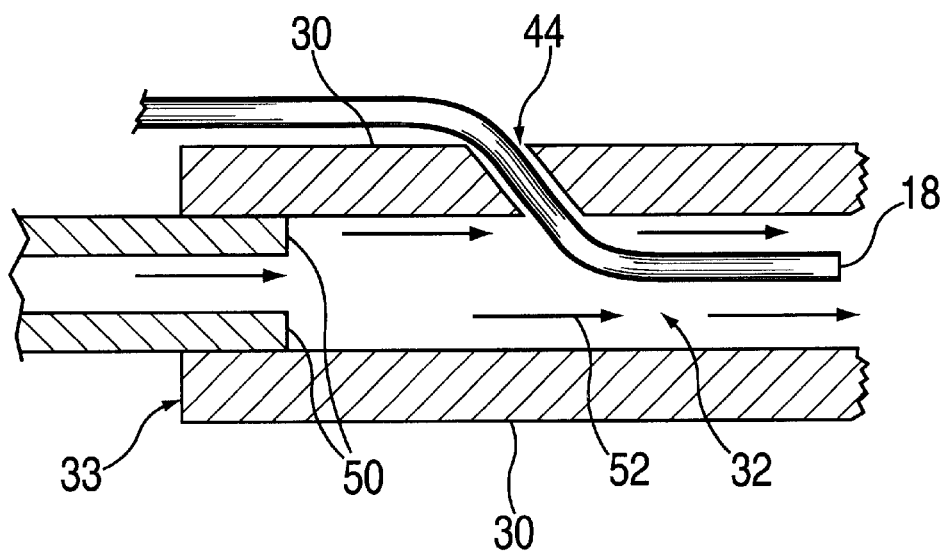
FIG. 9 is a cross-sectional view of the installation of a wire lead through a hole in the tube of FIGS. 6, 7, 8 and an air pressure device.

FIG. 9 depicts the installation of a wire lead 6 into a tube 4A with holes 44. The terminal end 18 of the wire lead 6 is inserted from the exterior surface 30 through the hole 44 into the central cavity 32 away from the distal end. Advantageously, a pipe 50 is inserted in the distal end 33 and supplies a pressurized air flow 52 in the direction of the proximal end 31 of the tube. The pressurized air flow 52 entrains the wire lead 6 into the central cavity 32 and draws the wire lead 6 down the length of the tube 4 away from the distal end 33 stopping when the coiled electrode 20 reaches the hole 44.

Figure 10:
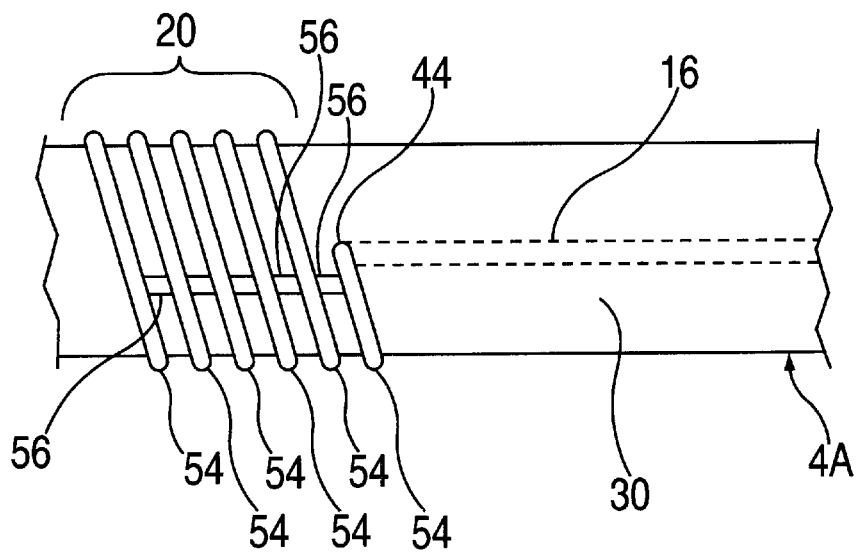
FIG. 10 depicts a knitted coil from an electrode catheter.

FIG. 10 shows a coiled electrode 20 extending out through a hole 44 with the insulated portion 16 of the wire lead within the tube 4A. In the completed assembly of the electrode catheter C, the coils 54 of the coiled electrode 20 are wrapped around the exterior surface 30 of the tube 4A. Each coil 54 of the coiled electrode 20 are knit together or otherwise connected by a cross-bar 56 to keep the coils 54 from separating from the tube and to keep the coils 54 wrapped tightly together. In once embodiment, the coils 54 are knitted to each other or fused with a heat source such as an eximer laser. Thus, the cross-bar 56 between the coils 54 is formed by welds or a fusing of the coils 54. In an alternative embodiment, the coils 54 are joined with an adhesive.

Figure 11:
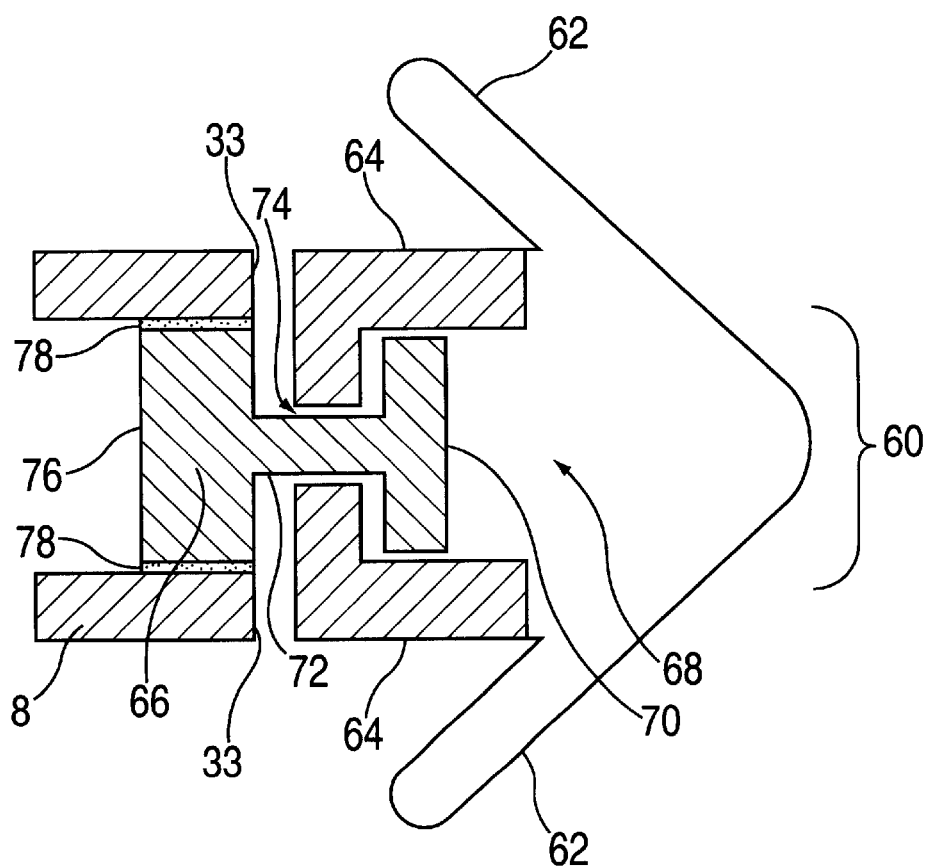
FIG. 11 is a cross-sectional view of the tip member of the electrode catheter.

FIG. 11 depicts a cross-sectional view of the tip member 12. The tip member serves as a cap for the end of the tube and as a surface for contact with the cardiac wall. Many possible versions of a tip member can be used. In the preferred embodiment, the tip member is comprised of a cardiac contact 60, two or more flexible tines 62, a mounting base 64 and a swivel connector 66. The mounting base 64 has a cylindrical chamber 68. The chamber 68 receives a round top portion 70 of the swivel connector 66 but is not affixed to permit the mounting base 64 to rotate around the top portion 70. A narrow cylindrical mid-portion 72 of the swivel connector 66 extends outward from the internal chamber 68 through a central round aperture 74 in the mounting base 64. A round bottom portion 76 of the swivel connector 66 having a diameter approximately the inside diameter of the tube is affixed within the distal end 33 of the tube with adhesive 78, or welded thereto.

Figure 12:
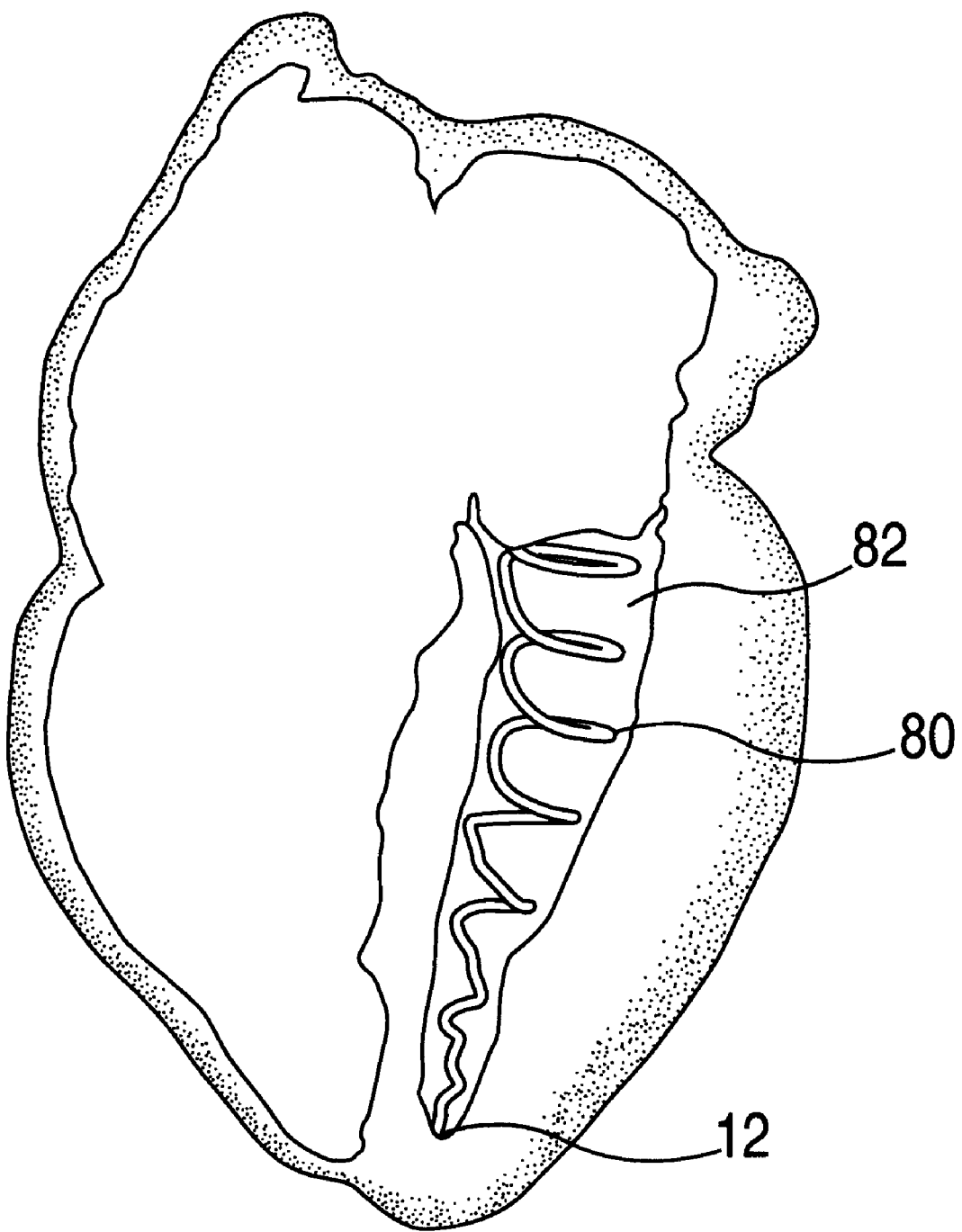
FIG. 12 shows one geometrically shaped embodiment of the electrode catheter within a cardiac chamber.

FIG. 12 shows a deployed electrode catheter 80. The electrode catheter 80 is disposed within the chamber 82 and is arranged in a geometric shape appropriate for the desired purpose, such as mapping the cardiac chamber 82. Generally the catheter 80 is shaped so that some or most of its electrodes are adjacent to or even touching the inner walls of the respective cardiac chamber.

FIG. 12 further shows the tip member 12 of the electrode catheter, after insertion into a cardiac chamber, engaging the cardiac wall. The flexible tines 62 provide a temporary means to stabilize the tip member on the cardiac wall. The swivel connector 66 allows the electrode catheter to be externally rotated while the tip member 12 maintains a stationary position. In this way, the electrode catheter can be used for various functions such as mapping, cardiac monitoring, pacing, and so forth.

Figure 13:
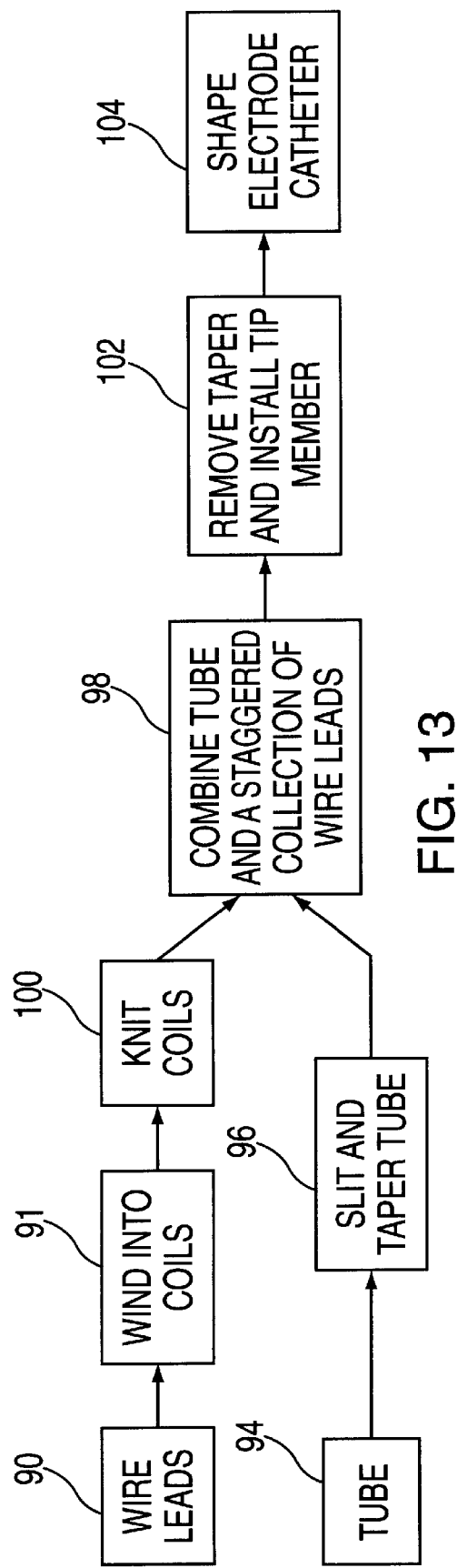
FIG. 13 is a flow chart depicting the steps in manufacturing the electrode catheter using a tube with a slit as shown in FIG. 4.
Figure 14:
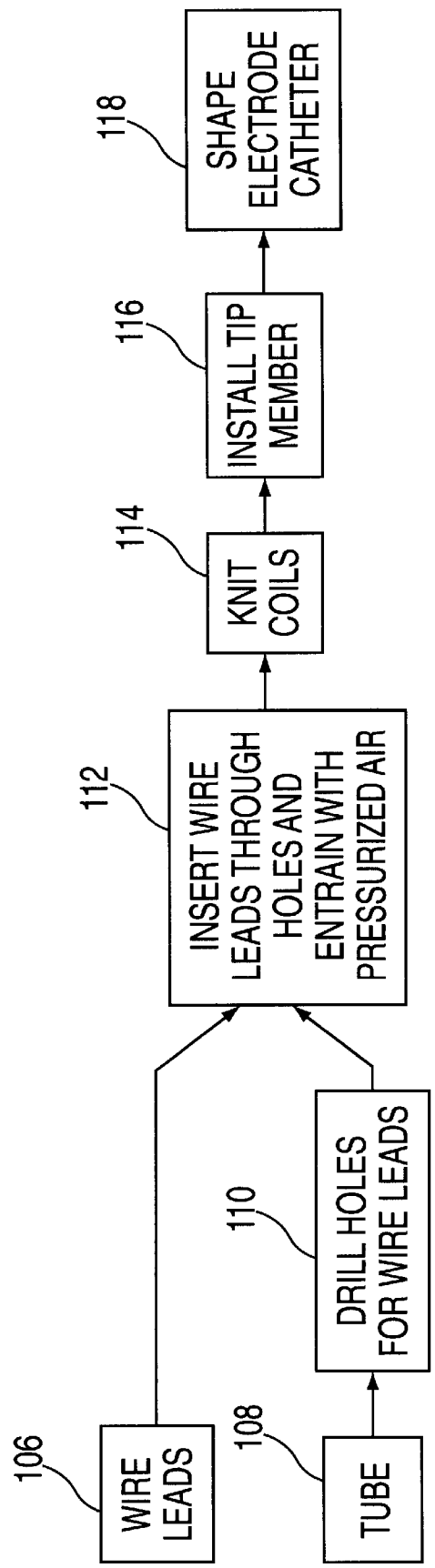
FIG. 14 is a flow chart depicting the steps in manufacturing the electrode catheter using a tube with holes as shown in FIGS. 6 and 7.

FIGS. 13 and 14 summarize the steps involved in the assembly of the preferred embodiments of the electrode catheter as heretofore described. FIG. 13 defines the steps involved in making the electrode catheter using the tube 4 with a slit depicted in FIG. 4. The assembly starts with forming the wire leads, step 90, and forming a tube, step 94. The wire leads are formed with the coiled electrodes by winding the wire leads into coils in step 91. Each exposed coiled electrode 20 is separately knitted, step 100, to join all of its coils 54. The tube 4 formed in step 94, is slit and tapered, step 96, as shown in FIG. 4. The slit and tapered tube, step 96, is then combined, step 98, with a staggered collection of wire leads so that the coiled electrodes 20 surround the exterior surface 30 of the tube 4 and the portion of the wire leads covered by insulated material 16 are contained within the cavity 32 of the tube 4. Next, the tapered end is severed and the tip member is installed, step 102. Finally, the electrode catheter is formed in a shaping process, step 104, into a geometric configuration appropriate for a cardiac chamber by inserting the electrode catheter into a jig and then heating the assembly until the electrode catheter will generally maintain the jig's configuration.

The steps in the assembly of the alternative embodiment of the electrode catheter using the tube of FIG. 6 or 7 are summarized in FIG. 14. The assembly process starts with wire leads 6, step 106, and a tube 4A, 4B, step 108. The wire leads 6 of step 106 may be pre-made with coiled electrodes or may be coiled into coiled electrodes during the insertion step 112. In a drilling step 110, angled holes for each wire lead are drilled into the tube. In an insertion step 112, each wire lead is entrained into the tube by inserting one terminal end 18 of a wire lead into each hole 44 and forcing the wire lead 6 down the length of the tube 4A, 4B with the assistance of a pressurized air flow 52 so that only the coiled electrode 20 extends from the hole 44. After each wire lead 6 is separately inserted, in a knitting step 114, each exposed coiled electrode 20 is separately knitted to join all of its coils 54. Next, the tip member is installed, step 116, and then the electrode catheter is given its shape, step 118, by means of heating the electrode catheter in a jig.

I claim:

1. An electrode catheter comprising:
    a plurality of wire leads, each wire lead having a continuous coiled electrode and an insulated portion; and
    a tube with an exterior surface and a central cavity;
    wherein said wire leads are arranged with said coiled electrodes' coils disposed about said exterior surface and said insulated portions are disposed in said cavity;
    wherein the coils of each said coiled electrode are interconnected.

2. The electrode catheter of claim 1 wherein each said coiled electrode has 1 to 10 coils.

3. The electrode catheter of claim 1 further comprising a distal end with a tip member connected to said distal end.

4. The electrode catheter of claim 3 wherein said tip member can swivel independent of said tube.

5. The electrode catheter of claim 4 wherein said tip member has at least two flexible tines.

6. The electrode catheter of claim 1 wherein said exterior surface has a longitudinal slit through which said coiled electrodes extend from said central cavity.

7. The electrode catheter of claim 1 wherein said exterior surface has holes through which said coiled electrodes extend from said central cavity.

8. The electrode catheter of claim 7 wherein said holes are at an angle with respect to a central axis running longitudinally within the said tube.

9. The electrode catheter of claim 8 wherein said angle is in the range of 15 to 90 degrees.

10. The electrode catheter of claim 8 wherein said angle is about 60 degrees.

11. The electrode catheter of claim 7 wherein said holes are disposed in a spiral pattern around said tube.

12. The electrode catheter of claim 1 comprising 4 to 128 wire leads.

13. The electrode catheter of claim 1 wherein said electrode catheter is conformed to a flexible shape for use within a cardiac chamber.

14. The electrode catheter of claim 1 wherein said coils of each electrode are welded to each other.

15. The electrode catheter of claim 1 wherein said coils of each electrode are connected to each other by an adhesive.

16. The electrode catheter of claim 1 further comprising a connecting bar that connects said coils to each other.

17. An electrode catheter comprising:
    a plurality of wire leads wherein each wire lead is continuous and has a coiled electrode, an insulated portion and a terminal end; and
    a tube with a proximal end, a distal end, an exterior surface and a central cavity and a plurality of staggered holes;
    wherein said insulated portions of said wire leads are disposed within said central cavity;
    wherein said coiled electrodes coil around said exterior surface of said tube near said distal end and said wire leads extend into said cavity through said holes; and
    wherein said terminal ends extend outwardly of said proximal end.

18. A method for manufacturing an electrode catheter comprising the steps of:
    preparing wire leads with each wire lead having a coiled electrode and an insulated portion;
    preparing a tube to receive said wire leads, said tube having an external surface; and
    inserting said wire leads on said tube so that said coil electrodes are on said external surface and said insulated portions are within said tube;
    further comprising the step of coupling the coils of each coiled electrode to each other.

19. The method of claim 18 further comprising the step of mounting a tip member on said tube.

20. The step of claim 18 wherein said coupling step is performed by fusing the coils together.

21. The step of claim 20 wherein said fusing is performed with an eximer laser.

22. The step of claim 18 wherein said coupling step is performed with an adhesive.

23. The method of claim 18 further comprising the step of forming the electrode catheter into a flexible geometric shape for use within a cardiac chamber.

24. The method of claim 23 wherein said shaping step is performed by heating said electrode catheter in a jig.

25. The method of claim 18 wherein said step of preparing said tube includes longitudinal slitting of said tube.

26. The method of claim 25 wherein said step of preparing said tube further includes the tapering of one end of said tube.

27. The method of claim 18 wherein said inserting step includes arranging the wire leads in a staggered configuration and inserting said configuration of wire leads into the tapered end of said tube while simultaneously passing said tapered end through said coiled electrodes.

28. The method of claim 18 wherein said step of preparing said tube includes the drilling of angled holes in the tube.

29. The method of claim 28 wherein said inserting step includes the insertion of said wire leads through said holes and entraining said wire leads down the length of said tube with a pressurized air or fluid flow.

30. A method of manufacturing an electrode catheter comprising the steps of:
    preparing wire leads with each wire lead having a coiled electrode, an insulated portion and a terminal end;
    preparing a tube with a longitudinal slit and a tapered end to receive said wire leads;
    combining said wire leads with said tube by staggering said wire leads into a collection of wire leads and inserting said collection of wire leads into said tapered end of said tube while simultaneously passing said tapered end through said coiled electrodes;

coupling the coils of each said coiled electrode;

attaching a tip member to said tube after removing said tapered end; and shaping said electrode catheter into a flexible geometric shape for use within a cardiac chamber.

31. A method of manufacturing an electrode catheter comprising the steps of:

preparing wire leads with each wire lead having a coiled electrode, an insulated portion and a terminal end;

preparing a tube with angled holes to receive said wire leads;

combining said wire leads with said tube by inserting said wire leads through said holes and entraining said wire leads down the length of said tube with a pressurized air or fluid flow;

coupling the coils of each said coiled electrode;

attaching a tip member to said tube; and shaping said electrode catheter into a flexible geometric shape for use within a cardiac chamber.

32. An electrode catheter comprising:

a plurality of wire leads, each wire lead having a continuous coiled electrode and an insulated portion; and a tube with an exterior surface and a central cavity and a plurality of holes disposed longitudinally along said outer surface, at least some of said holes being circumferentially offset from adjacent holes;

wherein said Wire leads are arranged with said coiled electrodes' coils disposed about said exterior surface, said insulated portions are disposed in said cavity and each said wire lead extends through one of said holes.

33. The electrode catheter of claim 32 wherein said holes are arranged in a spiral pattern on said external surface.

34. An electrode catheter comprising:

a plurality of wire leads, each wire lead having a continuous coiled electrode; and a tube with an exterior surface and a central cavity and a longitudinal slit extending through said exterior surface;

wherein said wire leads are arranged through said longitudinal slit with said coiled electrodes' coils disposed about said exterior surface and said insulated portions are disposed in said cavity.

35. An electrode catheter comprising:

a plurality of wire leads, each wire lead having a continuous coiled electrode and an insulated portion; and a tube with an exterior surface and a central cavity, wherein said exterior surface has holes through which said wire leads extend from said central cavity, said holes being formed at an angle of 15–90 degrees with respect to an axis running longitudinally through said tube.

36. The electrode catheter of claim 35 wherein said angle is about 60 degrees.

37. An electrode catheter comprising:

a plurality of wire leads, each wire lead having a continuous coiled electrode and an insulated portion; and a tube with an exterior surface and a central cavity;

wherein said wire leads are arranged with said coiled electrodes' coils disposed about said exterior surface and wherein said tube is made of a material that is flexible and has shape memory, said tube being preshaped to conform to the shape of a cardiac chamber.

38. A method for manufacturing an electrode catheter comprising the steps of:

preparing wire leads with each wire lead having a coiled electrode and an insulated portion;

preparing a tube to receive said wire leads; and joining said wire leads and said tube with said coil electrodes being on said external surface and said insulated portions are within said tube;

wherein said step of preparing said tube includes the drilling of angled holes in the tube, with said wire leads extending through said angled holes.

39. The method of claim 38 further comprising staggering said angled holes in a predetermined configuration.

40. The method of claim 38 wherein said step of preparing said tube includes drilling said holes in a spiral configuration.

41. A method for manufacturing an electrode catheter comprising the steps of:

preparing wire leads with each wire lead having a coiled electrode and an insulated portion;

preparing a tube to receive said wire leads, including forming said tube with a plurality of holes arranged in a staggered configuration along the length of the tube with some adjacent holes being circumferentially offset; and joining said wire leads and said tube with said coil electrodes being on said external surface and said insulated portions are within said tube, said wire leads extending through said holes.

42. A method for manufacturing an electrode catheter comprising the steps of:

preparing wire leads with each wire lead having a coiled electrode and an insulated portion;

preparing a tube to receive said wire leads, said tube having an external surface with a longitudinal slit; and joining said wire leads and said tube with said coil electrodes being on said external surface and said insulated portions are within said tube, said wire leads extending through said longitudinal slit.

43. A method for manufacturing an electrode catheter comprising the steps of:

preparing wire leads with each wire lead having a coiled electrode and an insulated portion;

preparing a tube to receive said wire leads; and joining said wire leads and said tube with said coil electrodes being on said external surface and said insulated portions are within said tube; and preshaping said tube to a shape conforming to the shape of a cardiac chamber.

44. The method of claim 43 wherein said step of preshaping includes heating said electrode catheter in a jig.

45. A method for manufacturing an electrode catheter comprising the steps of:

preparing wire leads with each wire lead having a electrode and an insulated portion;

preparing a tube to receive said wire leads; and joining said wire leads and said tube by entraining said insulated leads in a flow of fluid to force said insulated leads through said tube.

46. A method of manufacturing an electrode catheter comprising the steps of:

preparing wire leads with each wire lead having a coiled electrode, an insulated portion and a terminal end;

preparing a tube with a longitudinal slit and a tapered end to receive said wire leads;

combining said wire leads with said tube by staggering said wire leads into a collection of wire leads and inserting said collection of wire leads into said tapered end of said tube while simultaneously passing said tapered end through said coiled electrodes;

coupling the coils of each said coiled electrode; and attaching a tip member to said tube after removing said tapered end.

47. A method of manufacturing an electrode catheter comprising the steps of:

preparing wire leads with each wire lead having a coiled electrode, an insulated portion and a terminal end;

preparing a tube with angled holes to receive said wire leads;

combining said wire leads with said tube by inserting said wire leads through said holes and entraining said wire leads down the length of said tube with a pressurized air or fluid flow;

coupling the coils of each said coiled electrode; and attaching a tip member to said tube.

* * * * *